United States Patent [19]

Messerschmidt et al.

[11] Patent Number: 4,877,960
[45] Date of Patent: Oct. 31, 1989

[54] MICROSCOPE HAVING DUAL REMOTE IMAGE MASKING

[75] Inventors: Robert G. Messerschmidt; Donald W. Sting, both of Stamford, Conn.

[73] Assignee: Spectra-Tech, Inc., Stamford, Conn.

[21] Appl. No.: 293,549

[22] Filed: Jan. 4, 1989

Related U.S. Application Data

[63] Continuation of Ser. No. 15,315, Feb. 17, 1987, abandoned.

[51] Int. Cl.$^4$ .......................... G01J 3/08; G01N 21/00; G01N 21/59; G01N 21/47
[52] U.S. Cl. ..................................... 250/341; 250/353; 250/347; 350/1.2; 350/526
[58] Field of Search ............... 250/341, 338, 330, 332, 250/353, 347; 350/1.2, 502, 504, 505, 507, 509, 513–516, 523–527

[56] References Cited

U.S. PATENT DOCUMENTS

| | | | |
|---|---|---|---|
| 2,657,969 | 9/1953 | Thor | 350/502 |
| 2,775,159 | 12/1956 | Frommer . | |
| 2,847,162 | 8/1958 | Meyer . | |
| 2,910,913 | 11/1959 | Michel | 350/502 |
| 3,013,467 | 12/1961 | Minsky . | |
| 3,052,168 | 9/1962 | Reed . | |
| 3,421,806 | 1/1969 | Weber . | |
| 3,518,014 | 6/1970 | Weber . | |
| 3,547,512 | 12/1970 | Baer . | |
| 3,594,087 | 7/1971 | Miranda . | |
| 3,623,809 | 11/1971 | Diprose et al. . | |
| 3,664,751 | 5/1972 | Haas . | |
| 3,705,755 | 12/1972 | Baer . | |
| 3,798,435 | 3/1974 | Schindl | 350/526 |
| 3,802,784 | 4/1974 | Reynolds et al. . | |
| 3,926,500 | 12/1975 | Frosch et al. . | |
| 3,933,408 | 11/1976 | Reinert | 350/523 |
| 4,113,344 | 9/1978 | Shoemaker | 350/526 |
| 4,148,552 | 4/1979 | Suzuki et al. | 350/526 |
| 4,170,398 | 10/1979 | Koester . | |
| 4,198,571 | 4/1980 | Sheppard . | |
| 4,323,299 | 4/1982 | Roberts . | |
| 4,478,482 | 10/1984 | Koester . | |
| 4,551,023 | 11/1985 | Nakauchi . | |
| 4,594,509 | 6/1986 | Simon et al. . | |
| 4,619,503 | 10/1986 | Reinheimer et al. . | |
| 4,653,880 | 3/1987 | Sting et al. . | |

OTHER PUBLICATIONS

NANOSPEC/10 Computerized Microspectrophotometer System—brochure.
The NanoSpec/20IR Computerized Infrared Microspectrophotometer—brochure.
The New Digilab Micro/IR40 Spectrometer—brochure.
Microscope Photometer—publication.
Clair et al., *Optik*, 64, No. 2, (1983) pp. 133–141.
Sheppard et al., *Optik* 55, No. 4 (1980) pp. 331–342.
Sheppard, et al., *Proc. R. Soc. Lond.* A 379, 145,158 (1982).
Sheppard, et al., *Optik* 58, No. 4 (1984), pp. 371–380.
*Micro-FTIR Spectrophometers and FTIR Microscopes*, brochure.

*Primary Examiner*—Jon W. Henry
*Attorney, Agent, or Firm*—Calfee, Halter & Griswold

[57] ABSTRACT

A universal microscope for use with a commercial FT-IR spectrophotometer comprises a visible light microscope for selecting and masking an area of a sample and an infrared microscope for sampling the masked area. The visible light microscope and the infrared microscope share a common optical path between one or more remote sample image plane masks and the sample plane such that both the visible light and the infrared radiant energy are masked twice to spatially define the same area at the sample plane. The first sample image plane mask removes energy from outside the target area at the sample focus. The second sample image plane mask removes energy from outside the target area that is diffracted by the first mask or the focusing optics. The first remote sample image plane is imaged onto the second remote image plane with the radiant energy gaining spectroscopic information and additional image information by passing through or reflecting off a sample located at the intervening sample plane. Samples having a diameter of less than 8 microns have been spectroscopically isolated with 2–25 micron infrared radiant energy.

8 Claims, 4 Drawing Sheets

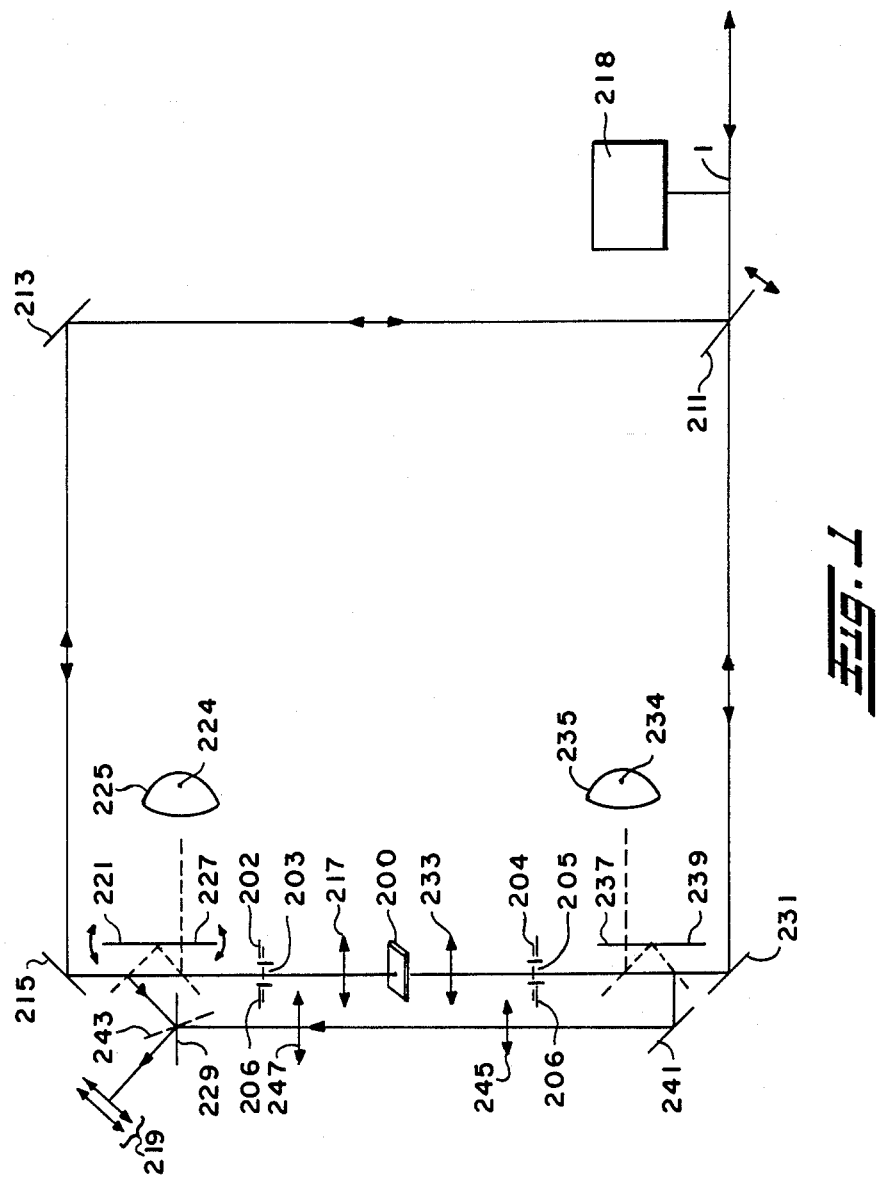

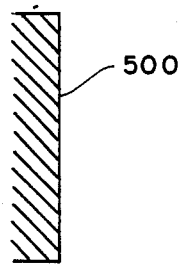
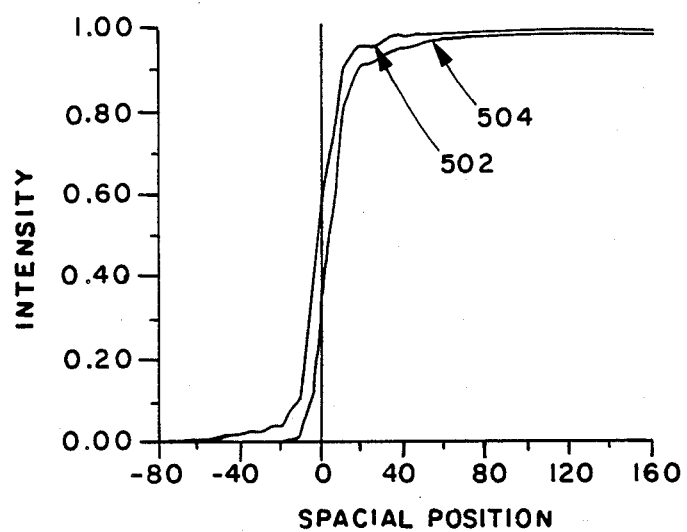
Fig. 3

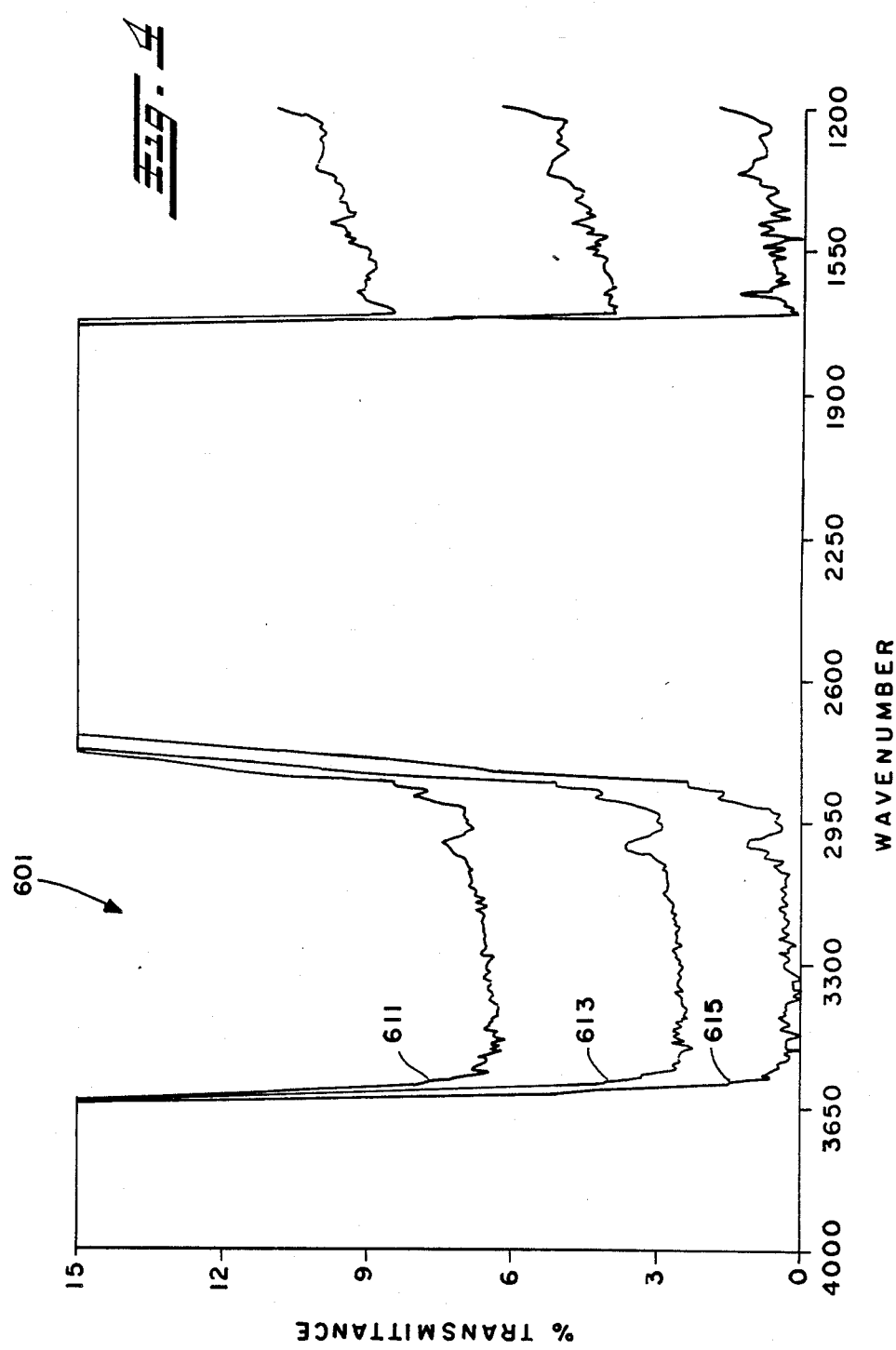

MICROSCOPE HAVING DUAL REMOTE IMAGE MASKING

This is a continuation of co-pending application Ser. No. 07/015,315 filed on Feb. 17, 1987.

BACKGROUND OF THE INVENTION

1. Field of the invention

The present invention relates to the general field of microscopy and particularly the field of Fourier-transform infrared (FT-IR) microspectrophotometry.

2. Description of related art

The ready existence of commercial FT-IR spectrophotometers greatly facilitates infrared analysis of specimens. The utility of FT-IR microspectroscopy, however, is limited by the size of the microscopic sample that can be observed. If a sample is too small, radiant energy from surrounding areas reaches the detector and produces a spectrum containing the combined features of all materials in the field of view of the microscope. This phenomenon is termed spectroscopic mixing and is a problem which is particularly acute for an infrared microscope because the longer wavelength of the infrared radiation results in lower inherent resolution as compared to, for example, a visible light microscope. Spectroscopic mixing may be eliminated by electronically subtracting the spectrum of a known material from a mixed spectrum. Electronic subtraction does not work, however, without first knowing both the spectral features and the relative intensity of the features for the area immediately surrounding the object of interest. As a practical matter, electronic subtraction often does not work because the spectrum of the surrounding material cannot be isolated.

The resolution of any microscope is limited by the effects of diffraction. Diffraction depends on the wavelength of the radiant energy, the numeric aperture of the optical system and the spatial coherence of the radiation. The smallest separation of objects that may be resolved is typically expressed in terms of Rayleigh's criterion which is mathematically defined as 0.61 times the wavelength of the radiant energy divided by the numerical aperture of the microscope. Diffraction, however, has long been recognized as a practical limit to resolution and not as a theoretical limit. Only the wavelength of the radiant energy ultimately need limit the resolution of a microscope.

Minsky U.S. Pat. No. 3,013,476, discloses what has come to be known in the art as a confocal scanning microscope. The confocal microscope uses two pinhole apertures positioned at focal planes. One pinhole aperture is placed between a light source and an objective lens at a real image plane so that the lens focuses the light emerging from the pinhole aperture onto a sample. A second pinhole aperture is positioned between an objective lens and a detector at a real image plane so that light from the sample is focused onto the second pinhole aperture. A sample is placed at the sample image plane and moved in a scanning pattern so that the detector supplies an input signal corresponding to the raster scan of a television. Minsky discloses that the confocal scanning microscope reduces the depth of field for an optically thick transmissive sample because the detector receives very little light from outside the plane of the sample image plane.

Others have noted that a confocal microscope increases the image contrast by reducing the amount of stray light that reaches the detector from outside the image plane. This superior depth of field resolution in a confocal microscope produces an apparent increase in resolution. Sheppard and Wilson of the University of Oxford have noted that a scanning confocal microscope may obtain an actual increase in the resolution above that anticipated for using the same optics without a confocal arrangement. This actual improvement in resolution, however, is only as great as a factor of 2.4 and is accompanied by a reduction in image contrast and, hence, a reduction in apparent resolution.

Experimental research in the field of confocal microscopy apparently has been directed to producing a scanning microscope for forming an image of a sample. The resolution of a scanning microscope is limited by the motion of the sample relative to the radiant energy. No known experiment has attempted to determine the actual point to point resolution of a confocal microscope.

Present mathematical models of image formation in a confocal microscope provide an inadequate explanation of image formation in the field of microspectrophotometry. The transform function for a confocal microscope involves a complicated convolution of the transform functions of the condensing and collecting optics as well as the focal plane apertures. The only exact mathematical solutions that have been published involve the special cases of point to point imaging of a point source that emits radiant energy that is either perfectly coherent or perfectly incoherent. Microspectrophotometry, however, necessarily involves the use of partially coherent radiant energy. The source of the radiant energy has effective spatial dimensions that are determined by the size and shape of the sample. The wavelength range of the radiant energy is determined by the wavelength range of the spectroscopic characteristics of the sample which are to be observed. The optical properties of a confocal microscope that uses partially coherent radiant energy is therefore important for microspectrophotometry and must be determined experimentally.

Practical concerns relating to throughput efficiency mitigate against using a confocal microscope in microspectroscopy. Conventional confocal microscopes have used a laser as an intense light source to supply monochromatic light to the source side pinhole aperture. However, conventional spectrometers, especially FT-IR spectrophotometers, do not have an intense source of constant amplitude radiant energy over a broad frequency range. Further, confocal microscopes have only attempted to image samples and not to distinguish between regions on a sample having different compositions. Thus, the theory of confocal microscopy and conventional confocal scanning microscopes have held no practical utility for microspectroscopy in general or for FT-IR microspectrophotometry in particular.

SUMMARY OF THE INVENTION

The present invention relates, first, to the discovery that a microscope can obtain an order of magnitude improvement in spatial definition of an observation area on a sample by masking the imaging energy at at least two remote sample image planes and, second, to a microscope for performing microscopy, particularly microspectrophotometry, in accordance with the discovery.

Specifically, a universal microscope for use in combination with a commercial FT-IR spectrophotometer comprises a visible light microscope for selecting and masking an area of a sample and an infrared microscope for spectroscopically analzing the masked area of the sample. The visible light microscope and the infrared microscope share a common optical path between one or more remote sample plane masks and a sample image plane such that both the visible light and the infrared radiant energy are masked twice, once when the radiant energy is incident to the surface of the sample and once when the radiant energy transmissively exits or is reflected from the sample, so as to spatially define the same area at the sample plane. The first remote sample image plane mask removes energy from outside the target area at the sample plane. The second remote sample image plane mask removes energy from outside the target area that was diffracted by the first mask or the condensing and collecting optics. The first remote sample image plane is effectively imaged onto the second remote sample image plane with the radiant energy regaining spectroscopic information and additional image information by passing through or reflecting off a sample located at an intervening sample image. The first and second remote sample image planes and the sample plane are thus conjugate image planes for both visible light and radiant energy plane.

The preferred embodiment of the present invention comprises a universal visible light and infrared microscope that easily switches between transmittance and reflectance modes in either upright or inverted configurations. A visual observation means permits a microscopist to observe a sample in reflectance mode simultaneously in both upright and inverted modes to as so properly mask a sample that is opaque to visible light but transparent to infrared radiant energy. A spectroscopist may thus select an observation area before directing the infrared energy beam of the FT-IR spectrophotometer at the selected sample area.

Experiments have shown that the spatial extent of the area at the sample plane defined by the mask in visible light is substantially the same area resolved by the infrared radiation even though the wavelength of the infrared radiation is approximately ten times greater than the wavelength of the visible light. The improvement in resolution obtained with partially coherent radiant energy exceeds anything predicted from theoretical investigations of the special cases of confocal imagery for point sources of perfectly coherent and perfectly incoherent radiation. Samples having a diameter of less than 8 microns have been spectroscopically isolated with 2-25 micron infrared radiant energy.

BRIEF DESCRIPTION OF THE DRAWINGS

FIG. 1 is a schematic layout of a universal microscope that places a sample plane between masked remote sample image planes according to the present invention;

FIG. 3 illustrates the diffraction pattern of masked microscope objectives using incoherent radiant energy; and FIG. 4 illustrates superimposed spectra comparing the effectiveness of masking at a remote sample image plane between the sample and the detector, to the effectiveness of masking at a remote sample image plane between the source and sample, to the effectiveness of masking at remote sample image planes on both sides of the sample.

DETAILED DESCRIPTION OF THE PREFERRED EMBODIMENTS

Figure 2A:
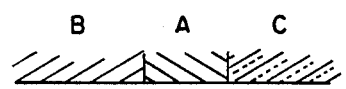
FIG. 2 principally illustrates radiant energy profiles in three contiguous sample materials and is useful for understanding the phenomenon of spectroscopic mixing and how the present invention overcomes the problem.

For purposes of the present invention, the phrase "radiant energy" describes invisible electromagnetic radiation used to observe a microscopic sample with an electronic detector. In contrast, the phrase "visible light" refers to electromagnetic radiation that in some way makes the sample visible to a microscopist. It is preferred that the visible light have a shorter wavelength than the radiant energy.

UNIVERSAL MICROSCOPE

FIG. 1 shows a universal microscope for use with the present invention. To simplify the drawing and aid in understanding the invention, condensing lenses are represented by outwardly pointing arrows and remote sample image planes are represented by dashed lines in a style that is generally known to those skilled in the art. A beam of invisible radiant energy 1 is incident on mode selecting mirror 211.

In a reflectance mode of operation, mirror 211 reflects radiant energy to mirrors 213 and 215. Mirror 215 directs the radiant energy to sample plane 200 through first focusing objective 217 which is preferably a Cassegrainian mirror lens. Before being focused on the sample plane 200, however, the microscope of the present invention focuses the radiant energy at a first remote sample image plane 202 that is physically remote from sample plane 200. A first variable aperture diaphragm or mask 203 spatially defines an arbitrary, adjustable geometric shape in the first remote sample image plane 202. First focusing objective 217 reimages the first remote sample image plane at the sample plane 200 to permit selecting the area on the sample plane that is illuminated by the incident radiant energy. For radiant energy reflected from the sample, first focusing optics 217 reimages the sample plane onto remote sample image plane 202 so that the first variable aperture diaphragm or mask 203 spatially defines the system aperture for both the incident and reflected radiant energy. First focusing objective 217 is thus operative to form an image of the mask at the sample plane or an image of the sample at the remote sample image plane.

In a transmittance mode, mode mirror 211 permits the radiant energy to travel directly from the source of radiant energy to mirror 231. The incident radiant energy is focused at second remote sample image plane 204. A second variable aperture diaphragm or mask 205 at the second remote sample image plane, spatially defines an arbitrary geometric shape. Second focusing objective 233, preferably a Cassegrainian mirror lens, reimages the second remote sample image plane onto the sample plane to permit selecting the area on the sample plane that is illuminated by the radiant energy. First focusing objective 217 focuses the radiant energy transmitted through sample plane 200 at first remote sample image plane 202. The first variable aperture diaphragm 203 at first remote sample image plane 202 spatially defines the shape of the illuminated area at the first remote sample image plane to correspond to the image of the second variable aperture diaphragm 205 at the second remote image plane. Mirrors 215, 213 and 211 direct the transmitted radiant energy to the detector 218.

The microscope shown in FIG. 1 permits the sample on sample plane 200 to be viewed in a variety of different modes. The microscope is operated in an inverse reflectance mode by positioning mirror 211 so that the beam of incident radiant energy is directed by mirror 231 through second remote sample image plane 204 and second focusing objective 233 onto the sample on sample plane 200. An appropriate beam splitter must be used to separate the incident and reflected radiant energy. Second focusing objective 233 collects the reflected radiant energy and directs it to the detector 218 using mirror 231. The microscope maybe operated in a transmissive/reflectance mode by directing the incident radiant energy to second focusing objective 233 and using first focusing objective 217 to collect radiant energy that is transmitted through the sample and second focusing objective 233 to collect radiant energy that is reflected from the sample. The microscope may be operated in an inverse transmissive/reflectance mode by directing the incident radiant energy to first focusing objective 217 using second focusing objective 233 to collect radiant energy that is transmitted through the sample and first focusing objective 217 to collect radiant energy that is reflected from the sample.

It is believed that the majority of the modes of operation using the radiant energy need not normally be used. Therefore, a microscope having only transmissive and reflectance modes of operation is preferred for reasons of mechanical simplicity and economy. The remaining modes, however, have utility in particular instances such as for easing sample handling and for checking the reliability of observations.

The shape of the transmissive area at first remote sample image plane 202 may be determined using a reflectance observation beam with eyepiece 219 which, in combination with flipper mirror 221 and flat mirror 229, provides means for visually observing the combined of both image sample plane 200 and first remote sample image plane 202. When partially transmissive mirror 227 is pivoted into the dashed line position shown in FIG. 1, visible light emanating from filament 224 of first lamp 225 is reflected by mirror 227 along a common optical path with the radiant energy. Flipper mirror 221 when pivoted to the dashed line position of FIG. 1 preferably blocks out the radiant energy so that sample image plane 202 and sample plane 200 are observed only with visible light emanating from first lamp 225 by way of a partially transmissive flipper mirror 227.

The sample plane may be viewed using a transmissive observation beam of visible light from filament 234 of second lamp 235. A partially transmissive mirror 237 may be pivoted into the path of the visible light to reflect the same toward second remote sample image plane 204 along a common optical path with the radiant energy. Second focusing objective 233 preferably images the visible light reaching second remote sample image plane 204 onto sample plane 200. First focusing objective 217 directs the visible light transmitted through the sample to first sample plane 202 and then to eyepiece 219 by way of mirrors 221 and 229.

The microscope shown in FIG. 1 can produce numerous additional observation beams of visible light. The microscope may receive an inverse reflectance observation beam from filament 234 of second lamp 235. Partially transmissive mirror 237 reflects part of the beam of visible light to sample plane 200. Mirror 239 when pivoted into the optical path directs the reflected light from the sample to mirror 241. Transfer optics 245 and 247 direct the reflected light visible to eyepiece 219 by way of mirror 243. Further, eyepiece 219 may be constructed with appropriate transfer optics so that the microscope may receive dual reflectance observation beams from lamps 225 and 235 which permit simultaneously observing the masking of remote sample image planes 202 and 204 with reflected light. The dual reflectance beam permits masking each remote sample image plane to the same shape when the sample is opaque to visible light but transmissive to the radiant energy. Additionally, first lamp 225 can produce an inverse transmissive observation beam using mirrors 227 and 239, simultaneously to view first and second remote sample image planes 202 and 204 and sample plane 200 when the sample is transmissive to visible light.

The optical path of the microscope is symmetric with respect to the optical path taken by the radiant energy or the visible light with respect to the sample plane 200. Thus, the microscope of the present invention easily converts from a conventional upright microscope into an inverted microscope as needed to make a particular measurement sample material analysis.

The preferred embodiment of the present invention uses entirely mirror optics at any place where the visible light and radiant energy share a common optical path. For example, most visible light transmissive materials used in microscopes are opaque to infrared light and, in any event, no refracting lens is known that can focus infrared radiant energy and visible light at the same remote sample image plane. Exact concurrence of the remote sample image planes formed with the radiant energy and visible light is necessary to mask a sample with visible light and then observe it with the radiant energy.

Adjustments to the focusing objective may be necessitated by optical distortions introduced by the sample. For example, it is known in the art that a sample may introduce spherical aberration into the observed image. This spherical aberration may be corrected by reducing the separation of the primary and secondary mirrors of focusing objectives 217 and 233 according to the formula:

$$Kt(n_i^2-1)/n_i^3;$$

where
t = thickness of the sample;
$n_i$ = index of refraction of the specimen; and
K = a constant unique to the microscope objective.
The derivation and use of this formula is understood by a person skilled in the art and, therefore, not a subject of the present invention.

DUAL REMOTE IMAGE MASKING

Figure 2B:
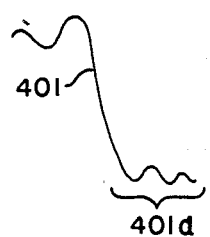
Figure 2C:
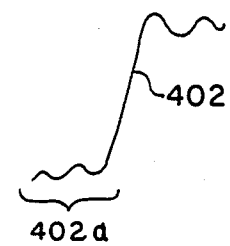
Figure 2D:
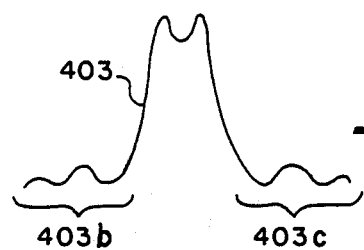

FIG. 2 illustrates the phenomenon of spectroscopic mixing that limits the resolution of a microspectrophotometer. FIG. 2a is a schematic representation of three sample materials, A, B and C. FIG. 2b shows profile 401 which represents the intensity of the radiant energy from region B. Part 401a of profile 401 represents the radiant energy diffracted into region A. Likewise, FIG. 2c shows profile 402 corresponds to the radiant energy from material C. Profile 402a represents the radiant energy from material C defracted into the area of material A. Finally, FIG. 2d shows profile 403 corresponding to the profile of the radiant energy from material A. Profiles 403b and 403c, represent radiant energy that is diffracted from the region of material A into the regions containing materials B and C, respectively.

The presence of extraneous energy from materials B and C in the field of view of material A causes the spectrum of material A to be mixed with the spectra of all three materials. This spectroscopic mixing may be corrected in several ways. The microscope of the present invention minimizes spectroscopic mixing through the spatial definition of a target region at the sample plane to correspond in shape to the shape of sample material A. Spatial definition means first removing radiant energy from outside the shape of a target by masking at a real image plane corresponding to the sample image plane and then removing radiant energy that is diffracted from within said shape by masking at a into regions outside said shape at a real image plane corresponding to said sample image plane. Defining the spatial extent of the incident radiation causes materials B and C to receive only energy from fringes 403b and 403c. Masking the sample a second time to a matched shape removes what energy has reached materials B and C and causes a substantial reduction in the spectroscopic mixing of the samples. Masking the radiant energy at remote image sample planes is preferred to "near field" masking at the surface of the sample because near field masking may destroy the sample. Remote sample image plane masking is also physically more convenient and produces superior optical performance for viewing inside an optically thick sample. The masking is initially performed by the spectroscopist using visible light, with the radiant energy thereafter passing through the adjusted masks for analyzing the targeted sample.

The spatial definition of a microscope using multiple real remote sample image plane masks is not determined in the same way as is resolution in a conventional microscope. The improvement in spatial definition as a percentage of illuminated target area is substantially independent of the wavelength of the radiant energy formed by the remote image plane mask so long as: (i) the masks at the respective remote sample image planes define the same geometric target area at the sample plane, and (ii) the smallest dimension of the target area is greater than the wavelength of the radiant energy. If these conditions are met, the geometric shape of the target region may be established using radiation having a short wavelength, such as visible lights and then observed with radiant energy having a longer wavelength, such as infrared energy without significantly enlarging the target area. Spatial definition may be limited by the contrast of the sample in the target area. A high contrast target sample diffracts more energy into adjacent regions than does a low contrast target since the amount of diffraction is proportional to the difference in the refractive indices between the adjoining materials. Masking more than two remote sample image planes does not appear to increase spatial definition although experimental evidence is not conclusive.

FIG. 3 illustrates the principles of diffraction that govern the present invention. FIG. 3a shows a diffraction edge 500. Profile 502 of FIG. 3b represents the distribution of diffracted energy in a microscope objective after it is masked once by edge 500 at a remote sample image plane using radiant energy from a perfectly incoherent point source. Profile 504 represents a corresponding profile for radiant energy from the first remote sample image plane that is also masked at a second remote sample image plane. The energy in the main diffraction lobe is pulled closer to the edge of the mask so that twice masking the radiant energy from remote sample image planes effectively reduces the relative amount of energy present in the diffraction fringes. If mask edge 500 is treated as a circular aperture, ninety five percent of the power contained in the radiant energy is typically included within the fourth or fifth diffraction minimum. For a microscope that is twice masked, however, the ninety five percent power threshold is within the first diffraction minimum.

It is known in the art that the location of the first diffraction minimum is nearer a diffraction edge for coherent radiation than for incoherent radiation. Therefore, coherent radiation is preferred. Nevertheless, spatial definition at remote sample image planes also improves the resolution of a microscope objective using incoherent radiation. The resolution obtained using partially coherent radiation also increases.

Another method for decreasing the spread of the main diffraction lobe is to apodize the microscope objective, especially the condenser. Apodization, however, transfers power into the diffraction fringes and greatly reduces throughput efficiency by blocking most of the aperture. The preferred embodiment of the present invention uses apodized objectives in the form of Cassegrainian mirror lenses that block only a small percentage of the incident radiation. Resolution might be improved by apodizing the objective to an even greater extent at the expense of a decrease in signal to noise. However, the signal to noise ratio produced by the present invention already requires using more sensitive infrared detectors than presently found on some commercial FT-IR spectrophotometers. Any increase in the resolution of the microscope that might be gained by apodizing the aperture is not considered to be worth the loss in throughput efficiency.

EXAMPLE

FIG. 4 shows an infrared transmission spectrum of a human hair obtained by twice masking the radiant energy at remote sample image planes, once for the incident radiant energy and once for transmitted radiant energy. The hair was placed at a sample plane and the infrared radiant energy transmitted through the hair was directed to a detector connected to the computer of an FT-IR spectrophotometer. The hair represents a high contrast sample that produces significant diffraction at the sample image plane. An absorption band 601 corresponds to a region in which human hair is known to exhibit total absorption of infrared radiant energy. Profile 611 corresponds to the spectrum obtained by adjusting, under visible light, a four-shutter, variable aperture diaphragm at a remote sample image plane positioned between the sample and the detector to define a rectangular cross section area on the remote sample image plane corresponding to the shape of the hair. The adjustable shutters of the masks are schematically illustrated at 206 in FIG. 1. The radiant energy underneath the curve between approximately 2950 and 3500 wave numbers corresponds to stray light from regions surrounding the hair. Next, profile 613 was obtained by masking, in the same manner, a remote sample image plane between the source and the detector. The amount of stray radiant energy reaching the sample was reduced. Thus, if only a single mask is being used at a remote sample image plane to spatially define the sample area, it is preferred that the mask be positioned in a remote sample image plane located between the source and the sample so as to target energy only at the spatially defined area. Nevertheless, approximately 3% of the radiant energy reaching the detector was from areas located outside the sample area on the sample image plane. Finally, profile 615 corresponds to the spectrum obtained by masking the transmitted infrared radiant energy at both remote sample image planes so that both masks define substantially the same area on the sample image plane. Profile 615 exhibits the total absorption anticipated in the absorption band.

The principles, preferred embodiments and modes of operation of the present invention have been described in the foregoing specification. The invention, which is intended to be protected herein should not, however, be construed as limited to the particular forms described herein as these are to be regarded as illustrative rather than restrictive. Variations and changes may be made by those skilled in the art without departing from the spirit of the invention. Accordingly, the foregoing detailed description should be considered exemplary in nature and not as limiting to the scope and spirit of the invention set forth in the appended claims.

What is claimed is:

1. A microscope for spectrometry to analyze samples comprising:
    radiant energy source means to provide an invisible radiant energy beam;
    a first light source means to provide a visible light beam;
    a sample plane containing a sample to be analyzed;
    means to direct either the invisible radiant energy beam in a sampling mode or the visible light beam in a viewing mode along a common optical path, such path spatially passing through the sample;
    a first remote sample image plane on the common optical path;
    a first mask located at the first remote sample image plane in the common optical path remote from the sample such that said invisible radiant energy beam passes through said first mask before impinging upon the sample;
    a first lens on the common optical path between said first mask and said sample plane to form an image of said sample at the remote sample image plane and an image of the mask at the sample plane;
    a viewing means located such that said first mask and said remote sample image plane are viewable from the invisible radiant energy source side of the sample;
    means to vary the size of the first mask during viewing in the viewing mode to spatially define the sample area to a selected targeted arbitrary shape;
    an invisible radiant energy detector operative in the sampling mode to detect invisible radiant energy passing from said radiant energy source through the first mask, as adjusted, and the first lens to the targeted arbitrary shape of the sample to provide analysis of the sample within the selected targeted arbitrarily shaped area;
    and a movable optical switching means to direct either invisible radiant energy from the sample to the detector in the sampling mode or visible light to the viewing means in the viewing mode.

2. A microscope as set forth in claim 1 further including means to direct reflected invisible radiant energy from the sample through the first mask, as adjusted, to the invisible radiant energy detector.

3. A microscope as set forth in claim 1 further comprising:
    a second remote sample image plane on the common optical path remote from the sample plane on the optically opposite side of the sample plane from the radiant energy source means;
    a second mask at the second remote image plane in the common optical path;
    a second lens on the common optical path between said second mask and said sample plane;
    a second visible light source means directing visible light along the common optical path through the second mask and second lens to the sample;
    means to vary the size of the second mask during viewing in the viewing mode to match the remote sample image to the selected targeted arbitrary shape; and
    a second movable optical switching means to switch between directing visible light from the second light source through said second mask to said sample and directing invisible radiant energy transmitted through the sample through the second lens through the second mask to the radiant energy detector.

4. A miscroscope for spectrometry to analyze samples comprising:
    radiant energy source means to provide an invisible radiant energy beam;
    a sample plane containing a sample to be analyzed;
    a first visible light source means on a first side of the sample plane to provide a first visible light beam and a second visible light source means on the other second side of the sample plane to provide a second visible light beam;
    means to direct either the invisible radiant energy beam in a sampling mode or the first or second visible light beam in a viewing mode along a common optical path, such path spatially passing through the sample;
    a first remote sample image plane on the first side of the sample plane on the common optical path and a second remote sample image plane on the second side of the sample plane on the common optical path,
    a first lens on the common optical path between the sample plane and first remote sample image plane and a second lens on the common optical path between the sample plane and the second remote sample image plane, the first and second lens being operative to make the sample plane, the first remote sample image plane and the second remote sample image plane into optically focused image planes of one another for both visible light and invisible radiant energy;
    a first mask on the common optical path in the first remote sample image plane and a second mask on the common optical path in the second remote sample image plane;
    means to vary the size of either one of the masks while viewing in the viewing mode using either or both of the first and second visible light source means to spatially define the sample image to a selected targeted arbitrary shape and to then vary the size of the other of said masks while viewing in the viewing mode using either or both of the first and second visible light source means to match the sample image thereat to the selected targeted arbitrary shape;

viewing means to view the sample plane, the first remote sample image plane and the second remote sample image plane simultaneously and along the common optical path in the viewing mode;

a radiant energy detector operative in the sampling mode to detect the invisible radiant energy beam passing along the common optical path including passage through the sample;

and movable optical switching means to direct either the invisible radiant energy beam to the detector in the sampling mode or a visible light beam from either the first or second visible light sources to the viewing means in the viewing mode.

5. A method for illuminating and spectroscopically analyzing a sample material in a microscope comprising the steps of:

providing a source of visible light and a source of invisible radiant energy;

passing visible light along an optical path through a first remote sample image plane and first lens to a sample on a sample plane;

focusing the visible light at the first remote sample image plane and sample plane;

viewing along the optical path from the source side of the sample with visible light to observe images of the first remote sample image plane and sample;

adjusting a first mask in th remote sample image plane while viewing in visible light to target a sample area on the sample;

directing invisible radiant energy along the same optical path through the adjusted mask and lens to the sample; and transferring invisible radiant energy from the sample to a detector to analyze the sample.

6. The method set forth in claim 5 including the further step of reflecting the invisible radiant energy off the sample through the first mask, as adjusted, to the detector.

7. The method set forth in claim 5 including the further steps of:

transmitting visible light through the sample to a second lens and second remote sample image plane lying along the same optical path;

viewing the first and second remote sample image planes and sample in visible light;

adjusting a second mask in the second remote sample image plane to match the targeted sample area of the first mask; and transmitting invisible radiant energy through the first mask as adjusted, the first lens, the sample, the second lens and the second mask as adjusted to the detector.

8. The method of claim 5 including the further steps of:

providing a second visible light source;

passing light from the second visible light source along the optical path through a second remote sample image plane and second lens to the sample;

viewing along the optical path with visible light to observe the second remote sample image plane and sample as illuminated by the second visible light source;

adjusting a second mask in the second remote sample plane in visible light to match its size to the adjusted size of the first mask or vice versa; and transmitting invisible radiant energy through the first adjusted mask, first lens, sample, second lens and second adjusted mask to the detector or vice versa.

* * * * *